United States Patent
Karino

(10) Patent No.: US 10,231,663 B2
(45) Date of Patent: Mar. 19, 2019

(54) IMAGE DISPLAY CONTROL APPARATUS, IMAGE DISPLAY CONTROL METHOD, AND IMAGE DISPLAY CONTROL PROGRAM

(71) Applicant: FUJIFILM Corporation, Tokyo (JP)

(72) Inventor: Takatoshi Karino, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 38 days.

(21) Appl. No.: 15/452,455

(22) Filed: Mar. 7, 2017

(65) Prior Publication Data

US 2017/0258393 A1   Sep. 14, 2017

(30) Foreign Application Priority Data

Mar. 9, 2016   (JP) ................................ 2016-045495

(51) Int. Cl.
*A61B 5/00* (2006.01)
*A61B 6/00* (2006.01)
(Continued)

(52) U.S. Cl.
CPC .......... *A61B 5/4504* (2013.01); *A61B 5/0073* (2013.01); *A61B 5/055* (2013.01);
(Continued)

(58) Field of Classification Search
None
See application file for complete search history.

(56) References Cited

U.S. PATENT DOCUMENTS 5,291,537 A * 3/1994 Mazess ................... A61B 6/032
                                                              378/54
7,542,602 B2 * 6/2009 Hart ....................... A61B 6/461
                                                            382/132
(Continued)

FOREIGN PATENT DOCUMENTS

| JP | 2002-236910 A | 8/2002 |
|----|---------------|--------|
| JP | 2006-109959 A | 4/2006 |
| JP | 2007-526799 A | 9/2007 |
| JP | 2009-207727 A | 9/2009 |

OTHER PUBLICATIONS

Lecouvet et al., "Monitoring the response of bone metastases to treatment with Magnetic Resonance Imaging and nuclear medicine techniques: A review and position statement by the European Organisation for Research and Treatment of Cancer imaging group," European Journal of Cancer (2014) 50, 2519-2531.*
Mester et al., "Malignant Involvement of the Spine: Assessment by 18F-FDG PET/CT," J Nucl Med. Feb. 2004;45(2):279-84.*
Uchida et al., "18F-FDG PET/CT for Diagnosis of Osteosclerotic and Osteolytic Vertebral Metastatic Lesions: Comparison with Bone Scintigraphy," Asian Spine J 2013;7(2):96-103.*

(Continued)

*Primary Examiner* — Soo Shin
(74) *Attorney, Agent, or Firm* — Birch, Stewart, Kolasch & Birch, LLP

(57) ABSTRACT

An image display control apparatus includes: an image obtaining unit that obtains an image of a backbone region that includes at least a portion of the backbone of a subject; an emphasized display target region specifying unit that specifies an emphasized display target region within the backbone region based on the image; a bone metastasis region specifying unit that specifies an osteolytic metastasis region included in the backbone region; and a display control unit that causes images to be displayed by a display unit. The display control unit displays an osteolytic metastasis region that belongs within the emphasized display target region with a greater degree of emphasis than an osteolytic metastasis region outside the emphasized display target region.

12 Claims, 4 Drawing Sheets

(51) Int. Cl.
  *G06T 7/00* (2017.01)
  *A61B 5/055* (2006.01)
  *A61B 6/03* (2006.01)
  *G06T 11/00* (2006.01)
  *G06T 7/11* (2017.01)
  *G06T 7/174* (2017.01)

(52) U.S. Cl.
  CPC .............. *A61B 5/407* (2013.01); *A61B 5/742* (2013.01); *A61B 6/032* (2013.01); *A61B 6/461* (2013.01); *A61B 6/505* (2013.01); *G06T 7/0014* (2013.01); *G06T 7/0016* (2013.01); *G06T 7/11* (2017.01); *G06T 7/174* (2017.01); *G06T 11/001* (2013.01); *A61B 5/0082* (2013.01); *G06T 2207/10024* (2013.01); *G06T 2207/10081* (2013.01); *G06T 2207/10088* (2013.01); *G06T 2207/20081* (2013.01); *G06T 2207/20224* (2013.01); *G06T 2207/30012* (2013.01); *G06T 2207/30096* (2013.01)

(56) References Cited

U.S. PATENT DOCUMENTS

| | | | |
|---|---|---|---|
| 8,165,376 B2* | 4/2012 | Shen | G06T 7/0012 |
| | | | 382/129 |
| 8,194,959 B2* | 6/2012 | Sakaida | G06K 9/38 |
| | | | 382/128 |
| 2005/0197567 A1 | 9/2005 | Qian et al. | |
| 2013/0004043 A1* | 1/2013 | Ross | G06T 7/0016 |
| | | | 382/131 |
| 2013/0060302 A1* | 3/2013 | Polefko | A61N 1/36017 |
| | | | 607/46 |
| 2016/0148375 A1* | 5/2016 | Oh | G06T 11/008 |
| | | | 382/131 |

OTHER PUBLICATIONS

Rodallec et al., "Diagnostic Imaging of Solitary Tumors of the Spine: What to Do and Say," Radiographics. Jul.-Aug. 2008;28(4)1019-41.*
F Denis, "Spinal Instability as Defined by the Three-Column Spine Concept in Acute Spinal Trauma," Clin Orthop Relat Res. Oct. 1984;(189):65-76.*
Denis F., "The three column spine and its significance in the classification of acute thoracolumbar spinal injuries", Spine, 8 (8), pp. 817-831, 1983 (Abstract only).
Hammon et al., "Automatic detection of lytic and blastic thoracolumbar spine metastases on computed tomography", European Radiology 23 (7), pp. 1862-1870, 2013.
Sakamoto et al., "Temporal subtraction system for detecting bone metastasis using LDDMM: preliminary study", Int J CARS 9 (1), pp. S264-S265, 2014.

* cited by examiner

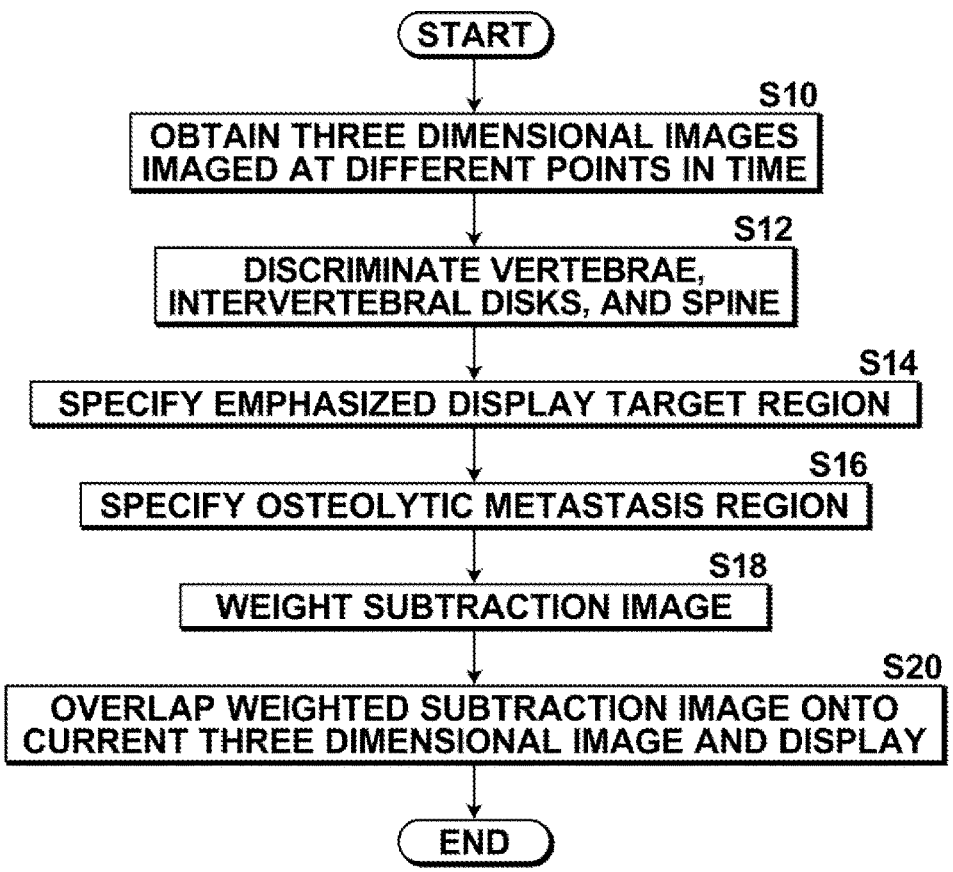
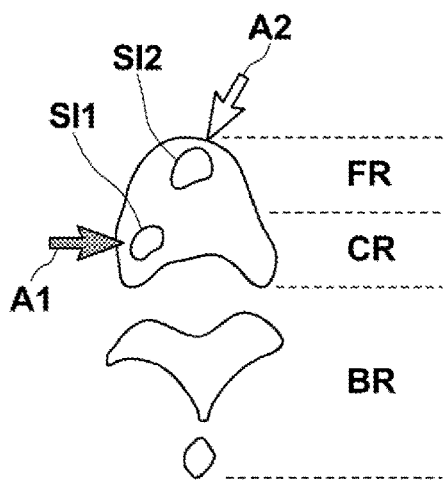

IMAGE DISPLAY CONTROL APPARATUS, IMAGE DISPLAY CONTROL METHOD, AND IMAGE DISPLAY CONTROL PROGRAM

CROSS REFERENCE TO RELATED APPLICATIONS

The present application claims priority under 35 U.S.C. § 119 to Japanese Patent Application No. 2016-045495 filed on Mar. 9, 2016. The above application is hereby expressly incorporated by reference, in its entirety, into the present application.

BACKGROUND

The present disclosure is related to an image display control apparatus, an image display control method, and an image display control program that display backbone osteolytic metastasis regions which are present in a backbone with emphasis.

Conventionally, various techniques have been proposed in which regions of interest to an observer are emphasized and displayed, when three-dimensional images which are obtained by CT (Computed Tomography) apparatuses or MRI (Magnetic Resonance Imaging) apparatuses are displayed on a monitor (refer to Japanese Unexamined Patent Publication Nos. 2002-236910, 2006-109959, and PCT Japanese Publication No. 2007-526799).

Meanwhile, various techniques that indicate and detect diseases of the bone (particularly bone metastasis) have been proposed. The purpose of these techniques is to assist diagnosis of bone metastasis by physicians (by preventing metastasis from being overlooked etc.).

For example, a technique in which temporally separated images which have been obtained by a CT apparatus are aligned, and differences between the images are obtained to indicate diseases of bones (particularly, bone metastasis) is proposed in R. Sakamoto, et al., "Temporal subtraction system for detecting bone metastasis using LDDMM: preliminary study", Int J CARS 9 (1), pp. S264-S265, 2014.

In addition, a technique in which classifiers which have learned bone metastasis regions of vertebrae by machine learning are employed to detect bone metastasis regions is proposed in M. Hammon, et al., "Automatic detection of lytic and blastic thoracolumbar spinal cord metastases on computed tomography", European Radiology 23 (7), pp. 1862-1870, 2013.

SUMMARY

Here, an important purpose of diagnosing bone metastasis is to find osteolytic metastasis at an early stage, and to prevent a decrease in QOL (Quality Of Life) due to fractured bones. If a region at which bone is present is dissolved due to osteolytic metastasis, the strength of the region will decrease. If the middle column of vertebrae is dissolved by osteolytic metastasis, the strength of this region will decrease, resulting in mechanical and neurological instabilities. That is, a case in which the middle column is dissolved is more dangerous than those in which the anterior column or the posterior column is dissolved. Taking the differences in the degrees of danger based on the diseased portion affected by osteolytic metastasis, and notifying physicians and the like of such information is clinically extremely important, as provision of such information will lead to osteolytic metastasis being overlooked being prevented, and to recognition of the degree of danger.

Note that Japanese Unexamined Patent Publication Nos. 2002-236910, 2006-109959, and PCT Japanese Publication No. 2007-526799, R. Sakamoto, et al., "Temporal subtraction system for detecting bone metastasis using LDDMM: preliminary study", Int J CARS 9 (1), pp. S264-5265, 2014, or M. Hammon, et al., "Automatic detection of lytic and blastic thoracolumbar spinal cord metastases on computed tomography", European Radiology 23 (7), pp. 1862-1870, 2013 do not propose a method for taking the differences in the degrees of danger based on the diseased portion affected by osteolytic metastasis, and notifying physicians and the like of such information.

The present disclosure has been developed in view of the foregoing circumstances. The present disclosure provides an image display control apparatus, an image display control method, and an image display control program which are capable of indicating the degree of danger of osteolytic metastasis to physicians and the like, and preventing osteolytic metastasis from being overlooked.

An image display control apparatus of the present disclosure comprises:

an image obtaining unit configured to obtain an image of a backbone region of a subject that includes at least a portion of the subject's backbone;

an emphasized display target region specifying unit configured to specify an emphasized display target region within the backbone region, based on the image;

a metastasis region specifying unit configured to specify an osteolytic metastasis region included in the backbone region; and a display control unit configured to display images on a display unit;

the display control unit displaying an osteolytic metastasis region that belongs within the emphasized display target region with a greater degree of emphasis than the osteolytic metastasis region outside the emphasized display target region.

In the image display control apparatus of the present disclosure, the image obtaining unit may obtain a plurality of images of the subject's backbone which are obtained at different points in time;

the bone metastasis region specifying unit may specify the osteolytic metastasis region by generating a subtraction image from the plurality of images; and the display control unit may display the osteolytic metastasis region that belongs within the emphasized display target region with a greater degree of emphasis than the osteolytic metastasis region outside the emphasized display target region, based on the subtraction image.

In addition, in the image display control apparatus of the present disclosure, the display control unit may administer different weighting on a subtraction image of an osteolytic metastasis region that belongs within the emphasized display target region and a subtraction image of an osteolytic metastasis region outside the emphasized display target region, to display the osteolytic metastasis region that belongs within the emphasized display target region with emphasis.

In addition, in the image display control apparatus of the present disclosure, the osteolytic metastasis region specifying unit may generate a score map that represents the probability of existence of an osteolytic metastasis region based on an image; and the display control unit may display the osteolytic metastasis region that belongs within the emphasized display target region with a greater degree of emphasis than the osteolytic metastasis region outside the emphasized display target region, based on the subtraction image, based on the score map.

In addition, in the image display control apparatus of the present disclosure, the osteolytic metastasis region specifying unit may specify an osteolytic metastasis region employing a classifier which is produced by machine learning, and generate a score map by mapping scores which are obtained when specifying the osteolytic metastasis region; and the display control unit may display the osteolytic metastasis region that belongs within the emphasized display target region with a greater degree of emphasis than the osteolytic metastasis region outside the emphasized display target region, based on the score map.

In addition, in the image display control apparatus of the present disclosure, the display control unit may administer different weighting on a score map of an osteolytic metastasis region that belongs within the emphasized display target region and a score map of an osteolytic metastasis region outside the emphasized display target region, to display the osteolytic metastasis region that belongs within the emphasized display target region with emphasis.

In addition, in the image display control apparatus of the present disclosure, the display control unit may display the osteolytic metastasis region that belongs within the emphasized display target region and the osteolytic metastasis region outside the emphasized display target region in different colors.

In addition, in the image display control apparatus of the present disclosure, the display control unit may display an indicator that indicates the osteolytic metastasis region that belongs within the emphasized display target region with more emphasis than an indicator that indicates the osteolytic metastasis region outside the emphasized display target region.

In addition, in the image display control apparatus of the present disclosure, the display control unit may display an indicator that indicates the osteolytic metastasis region that belongs within the emphasized display target region and an indicator that indicates the osteolytic metastasis region outside the emphasized display target region in different colors.

In addition, in the image display control apparatus of the present disclosure, the emphasized display target region specifying unit may specify the region of a middle column of the backbone as the emphasized display target region.

In addition, in the image display control apparatus of the present disclosure, the emphasized display target region specifying unit may divide the backbone to specify each of a region of a anterior column, a region of a middle column, and a region of a posterior column of the backbone, and then specify the region of the middle column as the emphasized display target region.

A display control method of the present disclosure comprises:

obtaining an image of a backbone region of a subject that includes at least a portion of the subject's backbone;

specifying an emphasized display target region within the backbone region, based on the image;

specifying an osteolytic metastasis region included in the backbone region; and displaying images on a display unit;

an osteolytic metastasis region that belongs within the emphasized display target region being displayed with a greater degree of emphasis than the osteolytic metastasis region outside the emphasized display target region.

An image display control program of the present disclosure causes a computer to function as:

an image obtaining unit configured to obtain an image of a backbone region of a subject that includes at least a portion of the subject's backbone;

an emphasized display target region specifying unit configured to specify an emphasized display target region within the backbone region, based on the image;

a metastasis region specifying unit configured to specify an osteolytic metastasis region included in the backbone region; and a display control unit configured to display images on a display unit;

the display control unit displaying an osteolytic metastasis region that belongs within the emphasized display target region with a greater degree of emphasis than the osteolytic metastasis region outside the emphasized display target region.

The image display control apparatus, the image display control method, and the image display control method of the present disclosure obtains an image of a backbone region of a subject that includes at least a portion of the subject's backbone; and specifies an emphasized display target region within the backbone region, based on the image. That is, a portion at which the presence of an osteolytic metastasis region is dangerous is specified as the emphasized display target region.

Next, an osteolytic metastasis region included in the backbone region is specified; and an osteolytic metastasis region that belongs within the emphasized display target region is displayed with a greater degree of emphasis than the osteolytic metastasis region outside the emphasized display target region. Thereby, the degree of danger of the osteolytic metastasis can be indicated to physicians and the like, and osteolytic metastasis which is greatly related to the patient's QOL can be prevented from being overlooked.

BRIEF DESCRIPTION OF THE DRAWINGS

FIG. 8 is a flow chart for explaining the operation of the medical image diagnosis assisting system that employs the image display control apparatus, the image display control method, and the image display control program according to the first embodiment.

FIG. 9 is a schematic diagram that illustrates an example in which subtraction images SI1 and SI2 are respectively indicated by arrow images A1 and A2, to be displayed with emphasis.

DETAILED DESCRIPTION OF THE PREFERRED EMBODIMENTS

Figure 1:
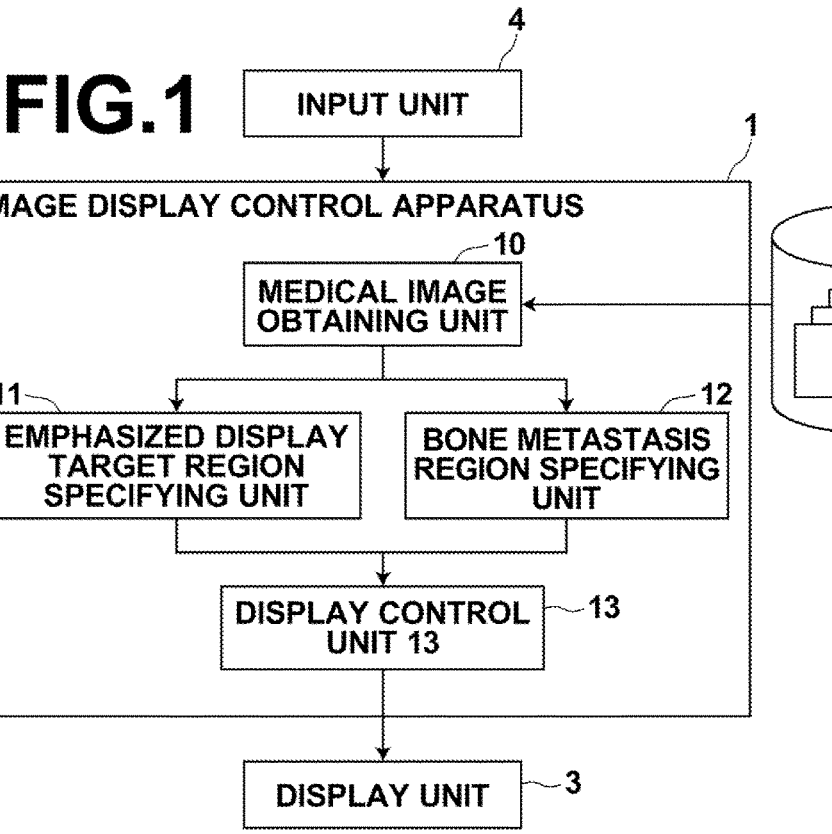
FIG. 1 is a block diagram that schematically illustrates the configuration of a medical image diagnosis assisting system that employs an image display control apparatus, an image display control method, and an image display control program according to a first embodiment.

Hereinafter, a medical image diagnosis assisting system that employs an image display control apparatus, an image display control method, and an image display control program according to a first embodiment will be described in detail with reference to the attached drawings. FIG. 1 is a block diagram that schematically illustrates the configuration of the medical image diagnosis assisting system of the present embodiment.

The medical image diagnosis assisting system of the present embodiment specifies an osteolytic metastasis region which is present in a backbone, specifies a region from within the osteolytic metastasis region which has a particularly high degree of danger, and emphasizes and displays the specified region. Hereinafter, the specific configuration of the medical image diagnosis assisting system will be described.

As illustrated in FIG. 1, the medical image diagnosis assisting system of the present embodiment is equipped with an image display control apparatus 1, a medical image storage server 2, a display unit 3, and an input unit 4.

The image display control apparatus 1 is a computer in which the image display control program of the present embodiment is installed. The image display control apparatus 1 is equipped with a CPU (Central Processing Unit), a semiconductor memory, and a storage device such as a hard disk or an SSD (Solid State Drive). The image display control program of the present embodiment is installed in the storage device. An image obtaining unit 10, an emphasized display target region specifying unit 11, a bone metastasis region specifying unit 12, and a display control unit 13 illustrated in FIG. 1 operate by the image display control program being executed by the CPU.

The image display control program is recorded on recording media such as a DVD (Digital Versatile Disc) and a CD-ROM (Compact Disc Read Only Memory) which are distributed, and installed onto the tablet terminal from the recording medium. Alternatively, the image display control program is stored in a recording device of a server computer connected to a network or in a network storage, in a state accessible from the exterior, downloaded to the computer according to a request, then installed therein.

The image obtaining unit 10 obtains three-dimensional images 6 which are imaged in advance. The three-dimensional images 6 are images of a patient which are imaged by a CT apparatus or an MRI apparatus, for example. In the present embodiment, two three-dimensional images 6 which are images of a backbone region that includes at least a portion of the patient's backbone imaged at different points in time are obtained. Then, a subtraction image is generated from the two three-dimensional images 6. As the two three-dimensional images 6 which are imaged at different points in time, a three-dimensional image 6 which was imaged in the past and a current three-dimensional image 6 which is imaged in the present may be obtained. Alternatively, two three-dimensional images 6 which were imaged in the past may be obtained. In the present embodiment, a past three-dimensional image 6 and a current three-dimensional image 6 are obtained.

Note that in the present specification, the term "backbone" is not limited to the entire backbone, but also encompasses a portion of a backbone that includes at least one vertebra. Similarly, the term "backbone region" is not limited to the region of the entire backbone, but also encompasses a region of a portion of a backbone that includes at least one vertebra.

In addition, the three-dimensional images 6 which are obtained may be volume data constituted by tomographic images such as axial tomographic images, sagittal tomographic images, and coronal tomographic images. Alternatively, tomographic images themselves may be obtained.

The three-dimensional images 6 are stored in the medical image storage server 2 in advance along with patient identifying data. The image obtaining unit 10 reads out three-dimensional images 6 having specified identifying data, based on patient identifying data which are input by a user employing the input unit 4 or the like, from the medical image storage server 2, and temporarily stores the read out three-dimensional images 6.

The emphasized display target region specifying unit 11 specifies an emphasized display target region within the backbone region, based on the current three-dimensional image 6 which is obtained by the image obtaining unit 10. Specifically, the emphasized display target region specifying unit 11 specifies a region of the middle column of the backbone region which is included in the three-dimensional image 6 as the emphasized display target region.

The middle column of the backbone is important in determining mechanical and neurological stability in connection with fractures of vertebrae. If the middle column is fractured, it will not be possible to support the axial load of the backbone, and there is a possibility that neurological impairment (particularly damage to the spinal cord) will occur. Fractures of the middle column are more dangerous than fractures of the anterior column or fractures of the posterior column (refer to D. Francis, "The three column spinal cord and its significance in the classification of acute thoracolumbar spinal injuries", *Spinal cord,* 8 (8), pp. 817-831, 1983).

Therefore, the present embodiment specifies the region of the middle column as the emphasized display target region. Hereinafter, a method by which the region of the middle column is automatically specified will be described with reference to FIG. 2.

First, the emphasized display target region specifying unit 11 performs a process to discriminate a plurality of vertebrae that constitute the backbone which is included within the current three-dimensional image 6. Known methods, such as a method that employs morphology calculations, a region expanding method based on a seed point, and the method disclosed in Unexamined Patent Publication No. 2009-207727 may be applied as the process for discriminating vertebrae. In addition, the emphasized display target region specifying unit 11 also discriminates a spinal cord and intervertebral disks, which are interposed among adjacent vertebrae. Known methods, such as the aforementioned region expanding method, may also be applied as the process for discriminating the intervertebral disks and the spinal cord.

Figure 2:
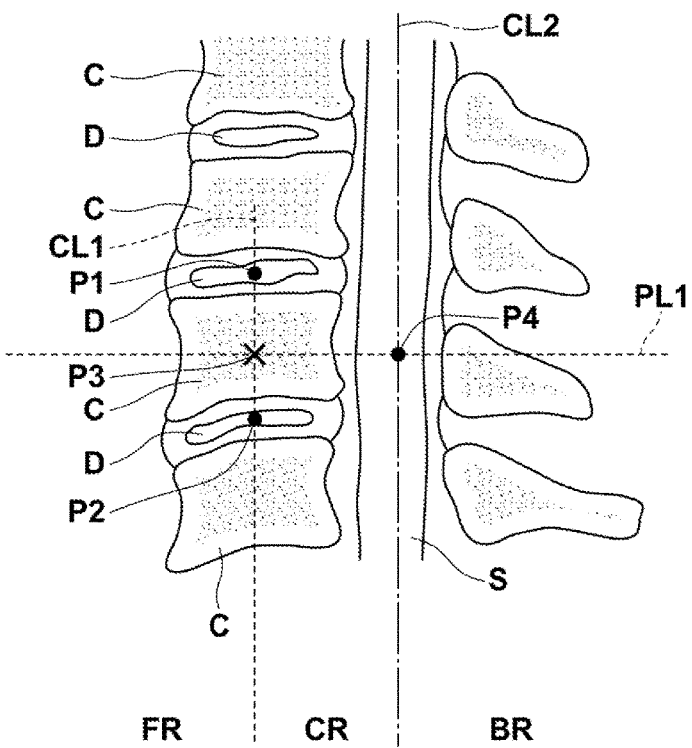
FIG. 2 is a diagram for explaining a method by which a middle column of vertebrae is specified as an emphasized display target region.

Next, the emphasized display target region specifying unit 11 sets an intersection point P1 between a center line CL1 of a centrum and an intervertebral disk D above a vertebra, and an intersection point P2 between the center line CL1 of a centrum C and an intervertebral disk D beneath a vertebra, as illustrated in FIG. 2. Note that the center line of the centrum C may be determined, for example, by connecting the centroids of each vertebra by spline interpolation or the like.

Next, a plane PL1 that passes through an intermediate point P3 and is perpendicular to a line that passes through the intersection point P1 and the intersection point P2 is set. Then, an intersection point P4 between the plane PL1 and a center line CL2 of the spinal cord S is determined. Note that the center line CL2 of the spinal cord S may be determined by detecting the spinal foramen (holes through which the spinal cord passes) of each vertebra with a detector, and by using spline interpolation on the center points of a plurality of the spinal foramen.

Next, a plane PL2 which is perpendicular to a line that passes through the intermediate point P3 and the intersection point P4, and which includes the intermediate point P3, is determined. In addition, a plane PL3 which is perpendicular to a line that passes through the intermediate point P3 and the intersection point P4, and which includes the intermediate point P4, is determined. Note that the plane PL2 and the PL3 are not illustrated in the drawings, but the plane PL2 includes a line that passes through the intersection point P1 and the intersection point P2, and extends in the thickness direction of the drawing sheet. In addition, the plane PL3 includes the intersection pint P4 and extends in the thickness direction of the drawing sheet. The plane PL2 and the plane PL3 are parallel. The vertebra is divided into three regions using the plane PL2 and the plane PL3 as boundaries. That is, a portion which is included in a region FR toward the abdomen with the plane PL2 as a boundary is designated as an anterior column, a portion which is included in a region BR toward the back with the plane PL3 as a boundary is designated as a posterior column, and a portion which is included in a region CR between the plane PL2 and the plane PL3 is designated as a middle column.

Figure 3:
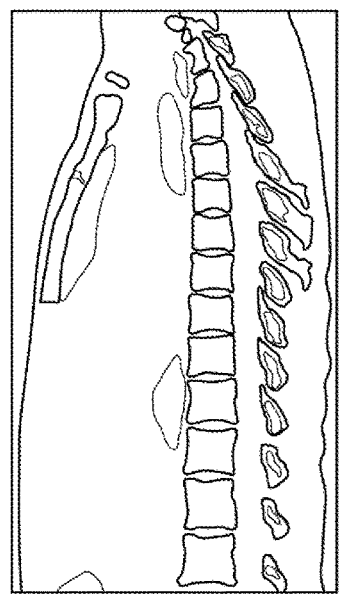
FIG. 3 is a schematic diagram that illustrates an example of a sagittal tomographic image of a backbone.
Figure 4:
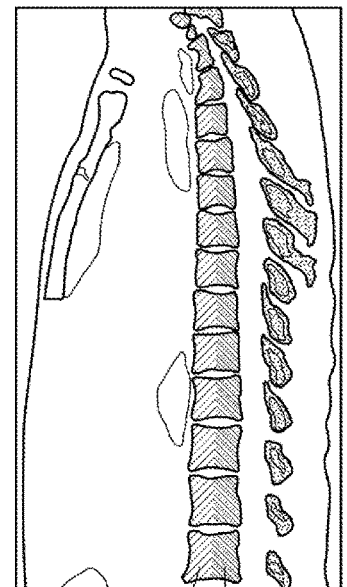
FIG. 4 is a schematic diagram that illustrates a region FR that includes a anterior column, a region CR that includes a middle column, and a region BR that includes a posterior column within a sagittal tomographic image.
Figure 5:
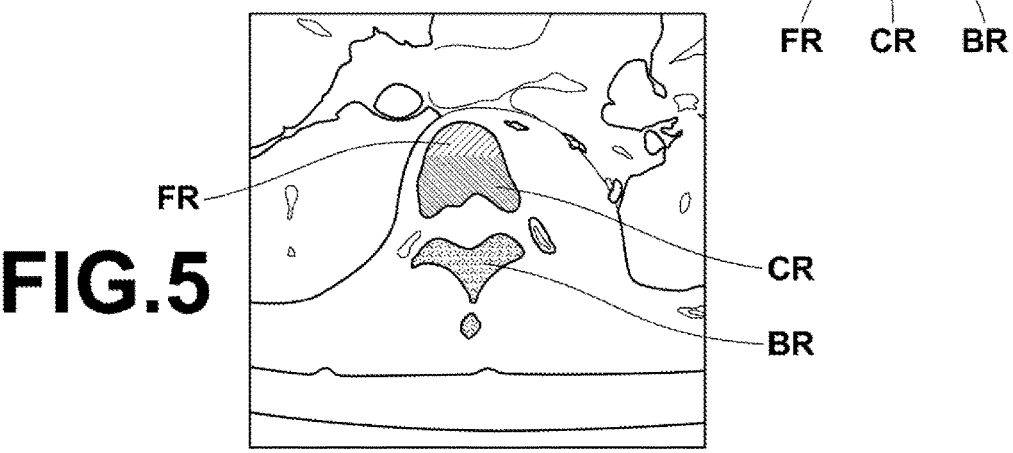
FIG. 5 is a schematic diagram that illustrates a region FR that includes a anterior column, a region CR that includes a middle column, and a region BR that includes a posterior column within an axial tomographic image.

FIG. 4 is a diagram that schematically illustrates an example in which a region FR that includes an anterior column, a region CR that includes a middle column, and a region BR that includes a posterior column are specified within the three-dimensional image 6 illustrated in FIG. 3 by the method described above. In addition, FIG. 4 illustrates the region FR that includes the anterior column, the region CR that includes the middle column, and the region BR that includes the posterior column specified within a sagittal tomographic image. However, regions FR, CR, and BR may also be specified within an axial tomographic image as illustrated in FIG. 5 as well.

Note that the region CR of the center region may be specified for each vertebra which is included in the three-dimensional image 6. Alternatively, the boundaries which are determined for one vertebra may be extended in the direction in which the backbone extends, to determine the boundaries for other vertebrae. In addition, in the case that the three-dimensional image 6 is volume data, the above method may be employed to determine the boundaries in a three dimensional space to specify the region of the middle column.

In addition, the method for specifying the region of the middle column is not limited to that described above, and the region of the middle column may be specified employing other algorithms. Specifically, the backbone region may be simply divided into three equal parts or three parts according to preset ratios along the direction in which the backbone extends, and the middle region may be designated as the region of the middle column.

The bone metastasis region specifying unit 12 specifies an osteolytic metastasis region which is included in the backbone region, based on the three-dimensional image 6 obtained by the image obtaining unit 10.

As described above, it can be said that a case in which the middle column is dissolved is more dangerous than those in which the anterior column or the posterior column is dissolved. Displaying the osteolytic metastasis region with emphasis, taking the differences in the degrees of danger based on the diseased portion affected by osteolytic metastasis into consideration, will lead to prevention of osteolytic metastasis being overlooked, and to recognition of the degree of danger.

Therefore, in the present embodiment, the osteolytic metastasis region is specified by the bone metastasis region specifying unit 12, and the region that belongs to the middle column within the osteolytic metastasis region is emphasized and displayed as a particularly dangerous region.

The bone metastasis region specifying unit 12 of the present embodiment generates a subtraction image from the current three-dimensional image 6 and the past three-dimensional image 6 which are obtained by the image obtaining unit 10, to specify the osteolytic metastasis region. Specifically, the bone metastasis region specifying unit 12 performs a process to align the current three-dimensional image 6 and the past three-dimensional image 6, and calculates the difference between the current three-dimensional image 6 and the past three-dimensional image 6 after the aligning process, to generate the subtraction image. A known method may be employed to generate the subtraction image. For example, the method disclosed in R. Sakamoto, G. Aoyama, K. Nakagomi, K. Fujimoto, M. Yakamil, T. Kubo, Y. Emoto, H. Sekiguchi, K. Sakai, C. Ceritoglu, M. I. Miller, M. Kawagishi, Y. Iizuka, S. Mori, H. Yamamoto, K. Togashi (2014) "Temporal subtraction system for detecting bone metastasis using LDDMM: preliminary study", *Int J CARS*, 9 (1), pp. S264-S265" may be employed.

The subtraction image which is generated by the bone metastasis region specifying unit 12 is an image in which an osteolytic metastasis region which was not present within the past three-dimensional image 6 but is present in the current three-dimensional image 6 is emphasized.

The display control unit 13 overlaps the subtraction image which is generated by the bone he metastasis region specifying unit 12 and the current three-dimensional image 6, and causes the display unit 3 to display the overlapped images. The display control unit 13 of the present embodiment displays the current three-dimensional image 6 in grayscale, and displays the subtraction image in color. The display control unit 13 assigns different colors to each pixel that constitutes the subtraction image according to the difference value thereof when displaying the overlapped images. More noticeable colors are assigned to pixels having greater difference values. Specifically, the display may be a gradation that changes from yellow to red, in which the red component becomes more pronounced as the difference value becomes greater, for example.

Further, the display control unit 13 administers different weighting on pixels that belong within the emphasized display target region and pixels outside the emphasized display target region when displaying the subtraction image. Specifically, the display control unit 13 multiplies the difference values of pixels that belong within the emphasized display target region by a weighting coefficient of "2", and multiplies the difference values of pixels outside the emphasized display target region by a weighting coefficient of "1". Thereby, the difference values of pixels that belong within the emphasized display target region are doubled. As a result, the emphasized display target region can be displayed with more emphasis than other regions. Note that the weighting coefficients are not limited to the above examples.

Here, osteolytic metastasis is a bone metastasis that dissolves bone. Therefore, the pixel values (CT values) of the osteolytic metastasis region will be low, because bone is dissolved therein. On the other hand, osteoblastic bone metastasis causes calcification of bone, and therefore the pixel values of osteoblastic bone metastasis regions will be high.

Accordingly, if a subtraction image is generated by subtracting a past three-dimensional image 6 from a current three-dimensional image 6, an osteolytic metastasis region will appear as negative difference values, whereas an osteoblastic metastasis region will appear as positive difference values.

In the present embodiment, it is desired for only the osteolytic metastasis region to be emphasized, from between osteolytic metastasis regions and osteoblastic metastasis regions. Therefore, the weighting operation described above is performed such that only the difference values of the osteolytic metastasis region become greater. That is, among the difference values of pixels within the emphasized display target region, only negative difference values are multiplied by "2" as a weighting coefficient, while positive difference values are multiplied by "1" as a weighting coefficient.

The osteolytic metastasis region is displayed as a gradation that changes from yellow to red according to the absolute value of the negative difference values, with the red component being more pronounced the larger the absolute value of the negative difference value is. The osteoblastic metastasis region is also displayed in color as a gradation that changes from light blue (small absolute value) to dark blue (large absolute value) according to the difference value, such that it is not as noticeable as the color display of the osteolytic metastasis region.

Figure 6:
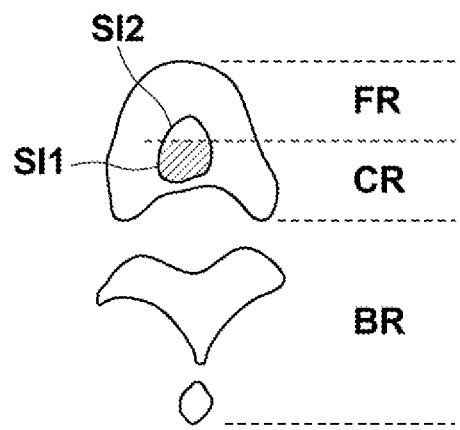
FIG. 6 is a schematic diagram that illustrates an example in which a temporal subtraction image is overlapped on an axial tomographic image and displayed.

FIG. 6 is a schematic diagram that illustrates an example in which a subtraction image, which is weighted in the manner described above, is overlapped on an axial tomographic image (a current three-dimensional image 6) and displayed. Note that here, an example in which only an osteolytic metastasis region is present, and an osteoblastic metastasis region is not present, is illustrated. In FIG. 6, a portion having a greater red component (a portion at which the absolute value of the difference value is great) is indicated by hatching. As illustrated in FIG. 6, the red component is more pronounced in the display of a subtraction image SI1 that belongs within the region CR of the middle column, while a subtraction image SI2 that belongs to the region FR of the anterior column is displayed in a color close to yellow. Note that the difference values within the subtraction images SI1 and SI2 are assumed to be substantially the same prior to the weighting operation.

Note that in the case that the osteolytic metastasis region (subtraction image) straddles the region CR of the middle column and the region FR of the anterior column as illustrated in FIG. 6, the degree of danger of the portion of the subtraction image SI2 may be indicated as being as high as the portion of the subtraction image SI1, and displayed in color employing the same weighting coefficient as that of the subtraction image SI1, in the case that the area of the subtraction image SI2 that belongs within the region FR of the anterior column is less than or equal to a threshold value which is set in advance, or the ratio of the area of the subtraction image SI2 that belongs within the region FR of the anterior column with respect to the area of the subtraction image SI1 that belongs within the region CR o the middle column is less than or equal to a threshold value which is set in advance.

Figure 7:
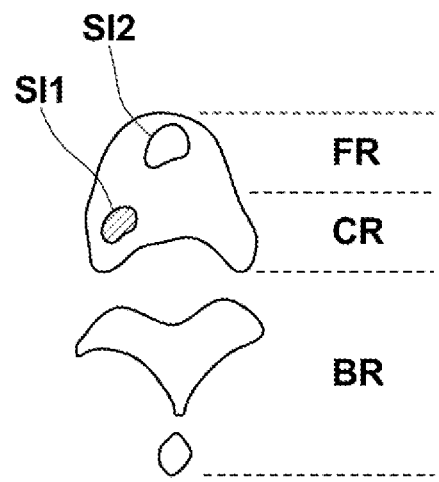
FIG. 7 is a schematic diagram that illustrates another example in which a temporal subtraction image is overlapped on an axial tomographic image and displayed.

In addition, FIG. 7 is a schematic diagram that illustrates an example of a manner of display in the case that an osteolytic metastasis region (subtraction image) is present in each of the region CR of the middle column and the region FR of the anterior column. In FIG. 7 as well, a portion having a more pronounced red component (a portion at which the absolute value of the difference value is great) is indicated by hatching. As illustrated in FIG. 7, the red component is more pronounced in the display of a subtraction image SI1 that belongs within the region CR of the middle column, while a subtraction image SI2 that belongs to the region FR of the anterior column is displayed in a color close to yellow. Note that the difference values within the subtraction image SI1 prior to the weighting operation and the difference values within the subtraction SI2 are assumed to be substantially the same in this case as well.

Note that the color display of the subtraction images is not limited to the above example, and may be any display method that draws an observer's attention as the absolute values of the difference values become greater. For example, colors of the same hue may be displayed with higher saturation or brightness as the absolute value of the difference value becomes greater.

The display unit 3 is equipped with a display device such as a liquid crystal display, and displays the three-dimensional images 6, the subtraction images, etc. Note that the display unit 3 corresponds to the display unit of the present disclosure.

The input unit receives input of various settings from users, and is equipped with input devices such as a keyboard and a mouse. The input unit 4 receives input of settings for patient identifying data, for example.

Note that the display unit 3 may function as the input unit 4 by employing a touch panel.

Next, the operations of the medical image diagnosis assisting system of the present embodiment will be described with reference to the flow chart illustrated in FIG. 8.

First, two three-dimensional images 6 of a patient which were imaged at different points in time are obtained by the image obtaining unit 10, based on input of patient identifying data by a user (step S10).

A current three-dimensional image 6 from between the two three-dimensional images 6 which are obtained by the image obtaining unit is input to the emphasized display target region specifying unit 11. The emphasized display target region specifying unit 11 discriminates vertebrae, intervertebral disks, and a spinal cord which are included in the current three-dimensional image 6, and specifies a region of a middle column as an emphasized display target region, based on the discriminated data (steps S12, S14).

Meanwhile, the two three dimensional images 6 which are obtained by the image obtaining unit 10 are input to the bone metastasis region specifying unit 12. The bone metastasis region specifying unit 12 performs a process to align a past three-dimensional image with the current three-dimensional image 6, then calculates the difference between the three-dimensional images 6 after the aligning process, to generate a subtraction image, and specifies an osteolytic metastasis region by the subtraction image (step S16).

Data regarding the region of the middle column specified by the emphasized display target region specifying unit 11 and the subtraction image generated by the bone metastasis region specifying unit 12 are input to the display control unit 13. The display control unit 13 performs the weighting operation described above to the difference value of each pixel that constitutes the subtraction image (step S18). Then, the display control unit 13 overlaps the weighted subtraction image on the current three-dimensional image 6, and performs color display of the overlapped subtraction image (step S20).

According to the medical image diagnosis assisting system of the present embodiment, the emphasized display target region is specified within the backbone region based on the three-dimensional image 6. That is, a portion at which it would be dangerous for an osteolytic metastasis region to be present is specified as the emphasized display target region.

The osteolytic metastasis region which is included in the backbone region is specified, and the osteolytic metastasis region that belongs within the emphasized display target region is displayed with a greater degree of emphasis than the osteolytic metastasis region outside the emphasized display target region. Thereby, the degree of danger of the osteolytic metastasis can be indicated to physicians and the like, and osteolytic metastasis which is greatly related to the patient's QOL can be prevented from being overlooked.

Next, a medical image diagnosis assisting system that employs an image display control apparatus, an image display control method, and an image display control program according to a second embodiment of the present disclosure will be described. The medical image diagnosis assisting system of the second embodiment differs from the medical image diagnosis assisting system of the first embodiment in the function of a bone metastasis region specifying unit 12.

In the first embodiment, the bone metastasis region specifying unit 12 specifies the osteolytic metastasis region by generating the subtraction image. In the second embodiment, the bone metastasis region specifying unit 12 specifies an osteolytic metastasis by using a classifier which has learned osteolytic metastasis regions of vertebrae by machine learning. Note that a subtraction image is not generated in the present embodiment, and therefore it is not necessary to obtain a past three-dimensional image.

Specifically, the bone metastasis region specifying unit 12 of the second embodiment scans a classifier which has been generated to be capable of discriminating osteolytic metastasis regions by a machine learning algorithm such as AdaBoost on a current three-dimensional image 6, to calculate a score that represents the likelihood that an osteolytic metastasis region is present for each pixel that constitutes the three-dimensional image 6. The osteolytic metastasis region is specified, by detecting a pixel position at which the score is maximal or equal to or greater than a threshold value which is set in advance. Note that a method for detecting bone metastasis regions using a classifier is disclosed in Hammon, Matthias; Dankerl, Peter; Tsymbal, Alexey: Wels, Michael; Kelm, Michael; May, Matthias; Suehling, Michael; Uder, Michael; and Cavallaro, Alexander, "Automatic detection of lytic and blastic thoracolumbar spinal cord metastases on computed tomography", *European Radiology*, 23 (7), pp. 1862-1870, 2013, for example.

The bone metastasis region specifying unit 12 of the present embodiment further generates a score map, in which scores which are obtained for each pixel are mapped. The score map is that in which the scores within the osteolytic metastasis region are higher than the scores within other regions. That is, the second embodiment employs the score map instead of the subtraction image which is employed in the first embodiment.

A display control unit 13 of the second embodiment overlaps a score map image, which is the score map generated by the metastasis region specifying unit 12 converted into a color image, onto the current three-dimensional image 6, and causes a display unit 3 to display the overlapped images.

The display control unit 13 assigns different colors to the score of each pixel that constitutes the score map according to the score when displaying the overlapped images. More noticeable colors are assigned to higher scores. Specifically, the display may be a gradation that changes from yellow to red, in which the red component becomes more pronounced as the score becomes greater, for example.

Further, the display control unit 13 administers different weighting on pixels that belong within the emphasized display target region and pixels outside the emphasized display target region when displaying the score map as a color image. Specifically, the display control unit 13 multiplies the scores of pixels that belong within the emphasized display target region by a weighting coefficient of "2", and multiplies the scores of pixels outside the emphasized display target region by a weighting coefficient of "1". Thereby, the scores of pixels that belong within the emphasized display target region are doubled. As a result, the emphasized display target region can be displayed with more emphasis than other regions. Note that the weighting coefficients are not limited to the above examples. In addition, the other components are the same as those of the first embodiment.

Note that the second embodiment specifies the osteolytic metastasis region by using the classifier which is generated by machine learning. However, the present disclosure is not limited to such a classifier, and a known filter process may be employed to specify an osteolytic metastasis region. For example, other learning or discriminating techniques similar to AdaBoost may be employed to specify the osteolytic metastasis region. Alternatively, cases which have been diagnosed as osteolytic metastasis may be collected, an average or common shape, density distribution, etc. of osteolytic metastasis regions may be obtained, and a filter that extracts regions having similar shapes and density distributions may be designed. The filter may be employed to search within new three-dimensional images 6, to automatically extract the presence and positions of osteolytic metastasis regions.

In addition, the first and second embodiments administer different weighting operations on the osteolytic metastasis region that belongs within the emphasized display target region and the osteolytic metastasis region outside the emphasized display target region. Alternatively, the weighting coefficient for the osteolytic metastasis region outside the emphasized display target region may be set to zero, such that osteolytic metastasis region outside the emphasized display target region is not displayed in color, thereby displaying the osteolytic metastasis region within the emphasized display target region with emphasis.

In addition, the first and second embodiments display the subtraction image or the score map image in color, to emphasize the display of the osteolytic metastasis region. However, the method by which the osteolytic metastasis region is emphasized is not limited to color display. For example, display of the osteolytic metastasis region may be emphasized by displaying an image of an arrow that indicates an osteolytic metastasis region or a frame image (bounding box) that indicates an osteolytic metastasis region.

In the case that indicators (arrows or frames) that indicate osteolytic metastasis regions are displayed in this manner as well, an indicator that indicates a region that belongs within an emphasized display target region within the osteolytic metastasis region is emphasized to a greater degree than an indicator that indicates an osteolytic metastasis region that belongs to a region other than the emphasized display target region.

FIG. 9 illustrates an example of emphasized display, in which subtraction images SD and SI2, which have been generated by the bone metastasis region specifying unit 12 of the first embodiment are indicated by arrow images A1 and A2, respectively. In this case, the arrow image A1 that indicates the subtraction image SI1, which belongs to the middle column region CR and is an emphasized display target region, is emphasized to a greater degree than the arrow image A2.

Specifically, the arrow image A1 may be displayed in color, and the arrow image A2 may be displayed in grayscale, for example. Alternatively, both the arrow image A1 and the arrow image A2 may be displayed in color. In this case, the arrow image A1 may be displayed in a more noticeable red color, while the arrow image A2 may be displayed as yellow or blue. As a further alternative, although FIG. 9 illustrates an example in which the arrow image A1 and the arrow image A2 are displayed at the same size, the arrow image A1 may be larger than the arrow image A2, to emphasize the display. As a still further alternative, the arrow image A1 may be displayed in a blinking manner, while the arrow image A2 is constantly displayed, to emphasize the display of the arrow image A1. As still yet another alternative, only the arrow image A1 may be displayed, without displaying the arrow image A2. That is, any display method maybe employed as long as the arrow image A1 draws the attention of an observer. Note that the same applies to cases in which frame images (bounding boxes) that indicate osteolytic metastasis regions are displayed as well.

What is claimed is:

1. An image display control apparatus, comprising:
a processor configured to:
obtain an image of a backbone region of a subject that includes at least a portion of the subject's backbone;
specify a region of a middle column of the backbone as an emphasized display target region within the backbone region, based on the image;
specify an osteolytic metastasis region included in the backbone region; and
display the image on a display;
the processor displaying the osteolytic metastasis region that belongs within the emphasized display target region with a greater degree of emphasis than the osteolytic metastasis region outside the emphasized display target region.

2. The image display control apparatus as defined in claim 1, wherein the processor is further configured to:
obtain a plurality of images of the subject's backbone which are obtained at different points in time;
specify the osteolytic metastasis region by generating a subtraction image from the plurality of images; and
display the osteolytic metastasis region that belongs within the emphasized display target region with a greater degree of emphasis than the osteolytic metastasis region outside the emphasized display target region, based on the subtraction image.

3. The image display control apparatus as defined in claim 2, wherein:
the processor is further configured to administer different weighting on the subtraction image of an osteolytic metastasis region that belongs within the emphasized display target region and the subtraction image of an osteolytic metastasis region outside the emphasized display target region, to display the osteolytic metastasis region that belongs within the emphasized display target region with emphasis.

4. The image display control apparatus as defined in claim 1, wherein the processor is further configured to:
generate a score map that represents a probability of existence of an osteolytic metastasis region based on the image; and
display the osteolytic metastasis region that belongs within the emphasized display target region with a greater degree of emphasis than the osteolytic metastasis region outside the emphasized display target region, based on the score map.

5. The image display control apparatus as defined in claim 4, wherein the processor is further configured to:
specify an osteolytic metastasis region employing a classifier which is produced by machine learning, and generates the score map by mapping scores which are obtained when specifying the osteolytic metastasis region; and
display the osteolytic metastasis region that belongs within the emphasized display target region with a greater degree of emphasis than the osteolytic metastasis region outside the emphasized display target region, based on the score map.

6. The image display control apparatus as defined in claim 4, wherein the processor is further configured to:
administer different weighting on the score map of an osteolytic metastasis region that belongs within the emphasized display target region and a score map of an osteolytic metastasis region outside the emphasized display target region, to display the osteolytic metastasis region that belongs within the emphasized display target region with emphasis.

7. The image display control apparatus as defined in claim 1, wherein the processor is further configured to:
display the osteolytic metastasis region that belongs within the emphasized display target region and the osteolytic metastasis region outside the emphasized display target region in different colors.

8. The image display control apparatus as defined in claim 1, wherein the processor is further configured to:
display an indicator that indicates the osteolytic metastasis region that belongs within the emphasized display target region with more emphasis than an indicator that indicates the osteolytic metastasis region outside the emphasized display target region.

9. The image display control apparatus as defined in claim 8, wherein the processor is further configured to:
display an indicator that indicates the osteolytic metastasis region that belongs within the emphasized display target region and an indicator that indicates the osteolytic metastasis region outside the emphasized display target region in different colors.

10. The image display control apparatus as defined in claim 1, wherein the processor is further configured to:
divide the backbone to specify each of a region of an anterior column, the region of a middle column, and a region of a posterior column of the backbone, and then specifies the region of the middle column as the emphasized display target region.

11. A display control method, comprising:
- obtaining an image of a backbone region of a subject that includes at least a portion of the subject's backbone;
- specifying a region of a middle column of the backbone as an emphasized display target region within the backbone region, based on the image;
- specifying an osteolytic metastasis region included in the backbone region; and
- displaying the image on a display unit;
- an osteolytic metastasis region that belongs within the emphasized display target region being displayed with a greater degree of emphasis than the osteolytic metastasis region outside the emphasized display target region.

12. A non-transitory computer readable recording medium having stored therein an image display control program, executable by a processor, to perform a method comprising:
- obtaining an image of a backbone region of a subject that includes at least a portion of the subject's backbone;
- specifying a region of a middle column of the backbone as an emphasized display target region within the backbone region, based on the image;
- specifying an osteolytic metastasis region included in the backbone region; and
- displaying the image on a display;
- wherein displaying images on a display includes displaying an osteolytic metastasis region that belongs within the emphasized display target region with a greater degree of emphasis than the osteolytic metastasis region outside the emphasized display target region.

* * * * *